US011253716B2

(12) United States Patent
Ogino et al.

(10) Patent No.: US 11,253,716 B2
(45) Date of Patent: Feb. 22, 2022

(54) DETECTION DEVICE AND ALARM SYSTEM HAVING THE DETECTION DEVICE

(71) Applicant: NIHON KOHDEN CORPORATION, Tokyo (JP)

(72) Inventors: Hirokazu Ogino, Tokyo (JP); Fumiyuki Matsumura, Tokyo (JP)

(73) Assignee: NIHON KOHDEN CORPORATON, Tokyo (JP)

( * ) Notice: Subject to any disclaimer, the term of this patent is extended or adjusted under 35 U.S.C. 154(b) by 131 days.

(21) Appl. No.: 16/079,748

(22) PCT Filed: Mar. 13, 2017

(86) PCT No.: PCT/JP2017/010033
§ 371 (c)(1),
(2) Date: Aug. 24, 2018

(87) PCT Pub. No.: WO2017/159635
PCT Pub. Date: Sep. 21, 2017

(65) Prior Publication Data
US 2019/0046036 A1    Feb. 14, 2019

(30) Foreign Application Priority Data

Mar. 15, 2016  (JP) .............................. JP2016-050647
May 23, 2016  (JP) .............................. JP2016-102663
Feb. 7, 2017  (JP) .............................. JP2017-020727

(51) Int. Cl.
*A61N 1/39*     (2006.01)
*G16H 40/67*   (2018.01)
(Continued)

(52) U.S. Cl.
CPC .......... *A61N 1/3993* (2013.01); *A61B 5/0022* (2013.01); *A61B 5/02438* (2013.01);
(Continued)

(58) Field of Classification Search
None
See application file for complete search history.

(56) References Cited

U.S. PATENT DOCUMENTS

| 5,544,661 A | 8/1996 | Davis |
| 6,161,036 A | 12/2000 | Matsumura et al. |

(Continued)

FOREIGN PATENT DOCUMENTS

| JP | H11-019057 A | 1/1999 |
| JP | 2001-078974 A | 3/2001 |

(Continued)

OTHER PUBLICATIONS

International Preliminary Report on Patentability issued in Patent Application No. PCT/JP2017/010033 dated May 25, 2018.

(Continued)

*Primary Examiner* — Kennedy Schaetzle
(74) *Attorney, Agent, or Firm* — Pearne & Gordon LLP (57) ABSTRACT

A detection device which, when an arrhythmia occurs, can prompt rapid taking of a countermeasure against the arrhythmia, and an alarm system having the detection device are provided. A portable detection device 10 has: a measuring section which can measure an electrocardiogram in a state where the section is applied to the body surface of the user; an analyzing section which analyzes whether the electrocardiogram contains an abnormal waveform indicating an arrhythmia or not; and a transmitting section which, if the analyzing section detects the abnormal waveform, transmits a detection signal indicating that the abnormal waveform is detected, to a communication terminal 20 around the user.

14 Claims, 8 Drawing Sheets

(51) Int. Cl.
    *A61B 5/00*     (2006.01)
    *G08B 21/04*     (2006.01)
    *A61B 5/318*     (2021.01)
    *A61B 5/361*     (2021.01)
    *A61B 5/024*     (2006.01)
    *G08B 21/02*     (2006.01)
    *G08B 25/00*     (2006.01)

(52) U.S. Cl.
    CPC .............. *A61B 5/318* (2021.01); *A61B 5/361* (2021.01); *A61B 5/7282* (2013.01); *A61B 5/742* (2013.01); *A61B 5/746* (2013.01); *A61B 5/747* (2013.01); *A61B 5/7465* (2013.01); *G08B 21/0453* (2013.01); *G16H 40/67* (2018.01); *A61B 5/7405* (2013.01); *G08B 21/02* (2013.01); *G08B 25/009* (2013.01)

(56) References Cited

U.S. PATENT DOCUMENTS

| | | | |
|---|---|---|---|
| 6,389,309 B1 | 5/2002 | Matsumura et al. | |
| 6,856,832 B1 | 2/2005 | Matsumura et al. | |
| 7,487,101 B1* | 2/2009 | Vasko | G16H 40/67 705/3 |
| 8,668,643 B2* | 3/2014 | Kinast | A61B 5/1116 600/300 |
| 2002/0103441 A1 | 8/2002 | Matsumura et al. | |
| 2002/0107453 A1 | 8/2002 | Matsumura et al. | |
| 2004/0127774 A1* | 7/2004 | Moore | G06F 19/3418 600/300 |
| 2005/0107714 A1 | 5/2005 | Matsumura et al. | |
| 2005/0119581 A1 | 6/2005 | Matsumura et al. | |
| 2005/0119582 A1 | 6/2005 | Matsumura et al. | |
| 2005/0143669 A1 | 6/2005 | Matsumura et al. | |
| 2007/0299473 A1* | 12/2007 | Matos | A61N 1/0476 607/5 |
| 2010/0231379 A1* | 9/2010 | Hutzler | A61B 5/411 340/539.12 |
| 2011/0112418 A1* | 5/2011 | Feild | G06F 19/3418 600/509 |
| 2011/0125040 A1* | 5/2011 | Crawford | A61B 5/335 600/509 |
| 2011/0270112 A1* | 11/2011 | Manera | A61B 5/04288 600/523 |
| 2012/0112903 A1 | 5/2012 | Kaib et al. | |
| 2012/0313760 A1 | 12/2012 | Okano | |
| 2013/0116533 A1* | 5/2013 | Lian | A61B 5/04012 600/391 |
| 2014/0152436 A1 | 6/2014 | Langer | |
| 2014/0155705 A1* | 6/2014 | Papadopoulos | A61B 5/0004 600/301 |
| 2015/0109125 A1 | 4/2015 | Kaib et al. | |
| 2016/0000349 A1* | 1/2016 | Sullivan | A61B 5/0452 600/509 |
| 2016/0071392 A1* | 3/2016 | Hankey | A61B 5/0205 340/573.1 |
| 2018/0110996 A1 | 4/2018 | Kaib et al. | |
| 2019/0091482 A1 | 3/2019 | Kaib et al. | |
| 2020/0114159 A1 | 4/2020 | Kaib et al. | |

FOREIGN PATENT DOCUMENTS

| | | |
|---|---|---|
| JP | 2002-219109 A | 8/2002 |
| JP | 2006-110180 A | 4/2006 |
| JP | 2012-254121 A | 12/2012 |
| JP | 2014-502448 A | 1/2014 |
| KR | 10-1206581 B1 | 11/2012 |
| KR | 2015-0000710 A | 1/2015 |
| WO | 2015/127218 A1 | 8/2015 |
| WO | 2016/010990 A2 | 1/2016 |

OTHER PUBLICATIONS

International Search Report issued in Patent Application No. PCT/JP2017/010033 dated Jun. 9, 2017.
Written Opinion issued in Patent Application No. PCT/JP2017/010033 dated Jun. 9, 2017.
Written Opinion of the International Preliminary Examining Authority issued in Patent Application No. PCT/JP2017/010033 dated Feb. 21, 2018.
Japanese Office Action issued in Japanese Patent Application No. 2017-020727 dated Nov. 10, 2020.
Japanese Office Action dated Jul. 27, 2021 issued in Patent Application No. 2017-020727.
European Office action dated Dec. 1, 2021 issued in EuropeanPatent Application No. 17 712 868.3.

* cited by examiner

DETECTION DEVICE AND ALARM SYSTEM HAVING THE DETECTION DEVICE

TECHNICAL FIELD

The present invention relates to a detection device which can detect an arrhythmia, and an alarm system which includes the detection device.

BACKGROUND ART

As a system for monitoring a person having concerns about a heart attack, for example, a medical telemeter system is known (JP-2001-78974-A).

SUMMARY

However, it is still the case that the life-saving rate for a heart attack due to an arrhythmia is low. For example, research reports that, among all cases of a heart attack in which a life-saving procedure was delayed, the rate of occasions in which the heart attack occurred at home is about 70%. This seems to be caused because there are many cases where, when a heart attack occurs due to an arrhythmia, persons (such as family members) surrounding the patient are not aware of the occurrence, and a procedure for saving the life is delayed, or no person is around the patient and the procedure is delayed.

It is an object of the invention to provide a detection device which, when an arrhythmia occurs, can prompt rapid taking of a countermeasure against the arrhythmia, and an alarm system having the detection device.

In order to attain the object, the detection device of the invention is a portable detection device, including:

a measuring section which can measure an electrocardiogram in a state where the section is applied to a body surface of a user;

an analyzing section which analyzes whether the electrocardiogram contains an abnormal waveform indicating an arrhythmia or not; and a transmitting section which, if the analyzing section detects the abnormal waveform, transmits a detection signal indicating that the abnormal waveform is detected, to a communication terminal around the user.

According to the configuration, when an arrhythmia occurs in the heart of the user to whom the detection device is attached, the detection device detects that the electrocardiogram under measurement contains an abnormal waveform indicating an arrhythmia, and transmits the detection signal to the communication terminal which is around the user. Even when the user is in a state where the user is difficult to perform communication because of the arrhythmia, therefore, it is possible to direct attention of a person around the user to the arrhythmia, and urge the person to rapidly take a countermeasure against the arrhythmia, through the communication terminal which receives the detection signal. Also with respect to an arrhythmia which is relatively hardly felt by the user oneself, it is possible to direct attention of a person around the user or the user oneself to the arrhythmia, and urge the person or the user to rapidly take a countermeasure against the arrhythmia.

The alarm system of the invention includes:
the above-described detection device; and
a communication terminal which is communicable with the detection device, and
the communication terminal has:
a receiving section which receives the detection signal transmitted from the transmitting section of the detection device; and
a terminal alarming section which, when the detection signal is received, issues an alarm.

According to the configuration, when an arrhythmia occurs in the heart of the user to whom the detection device is attached, the detection device detects that the electrocardiogram under measurement contains an abnormal waveform indicating an arrhythmia, and transmits the detection signal to the communication terminal which is around the user. The communication terminal which receives the detection signal issues an alarm to the surrounding area. Even when the user is in a state where the user is difficult to perform communication because of the arrhythmia, therefore, it is possible to direct attention of a person around the user to the arrhythmia, by means of the alarm issued by the communication terminal, and urge the person to rapidly take a countermeasure against the arrhythmia. Also with respect to an arrhythmia which is relatively hardly felt by the user oneself, it is possible to direct attention of a person around the user or the user oneself to the arrhythmia, and urge the person or the user to rapidly take a countermeasure against the arrhythmia.

According to the detection device and alarm system of the invention, it is possible to prompt rapid taking of a countermeasure against an occurring arrhythmia.

BRIEF DESCRIPTION OF DRAWINGS

FIG. 12 is a view illustrating the operation of the other modification of the alarm system.

DESCRIPTION OF EMBODIMENTS

Hereinafter, an embodiment will be described in detail with reference to the drawings.

Figure 1:
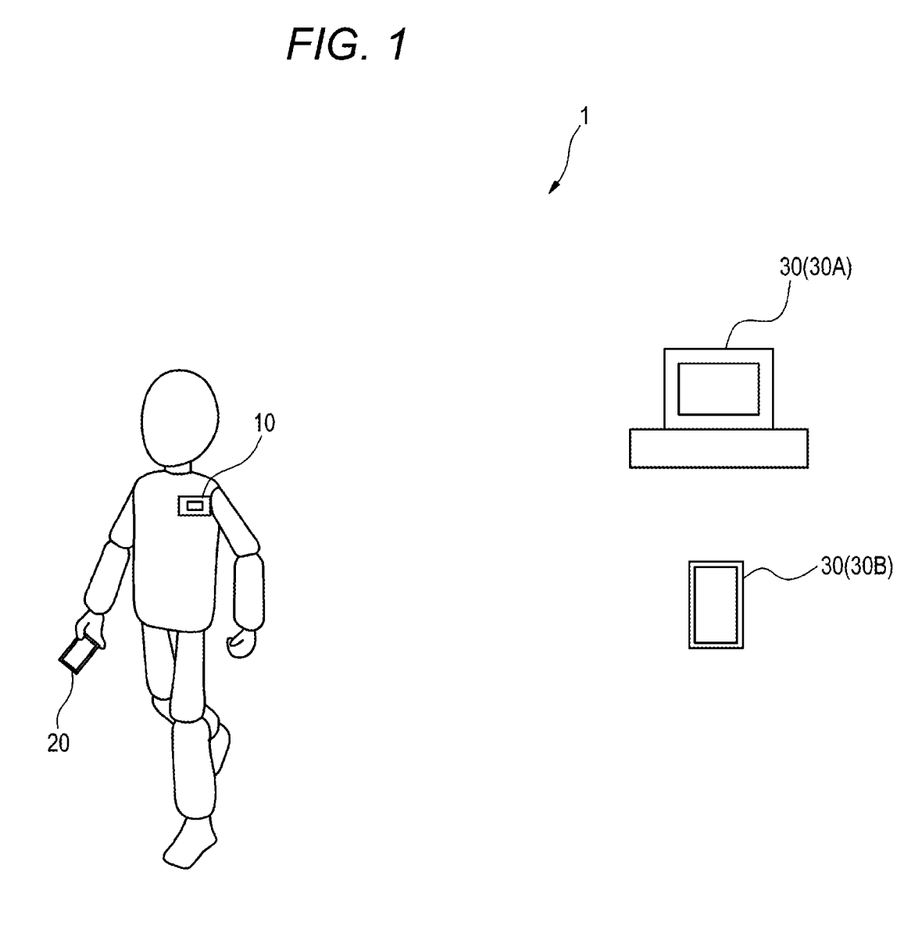
FIG. 1 is a system diagram of an alarm system which is an embodiment of the invention.

As shown in FIG. 1, an alarm system 1 includes: a detection device 10; a portable information communication terminal 20 (an example of the communication terminal) which is configured by a smart phone, a tablet, or the like; and terminal apparatuses 30 which are configured by a personal computer 30A, a portable information communication terminal 30B, and the like.

The detection device 10 can communicate with the information communication terminal 20 by using a short range wireless communication technique such as the NFC (Near Field Communication) or Bluetooth (registered trademark). For example, the information communication terminal 20 can communicate with the terminal apparatuses 30 which are remotely located, through a network such as the Internet.

Figure 2:
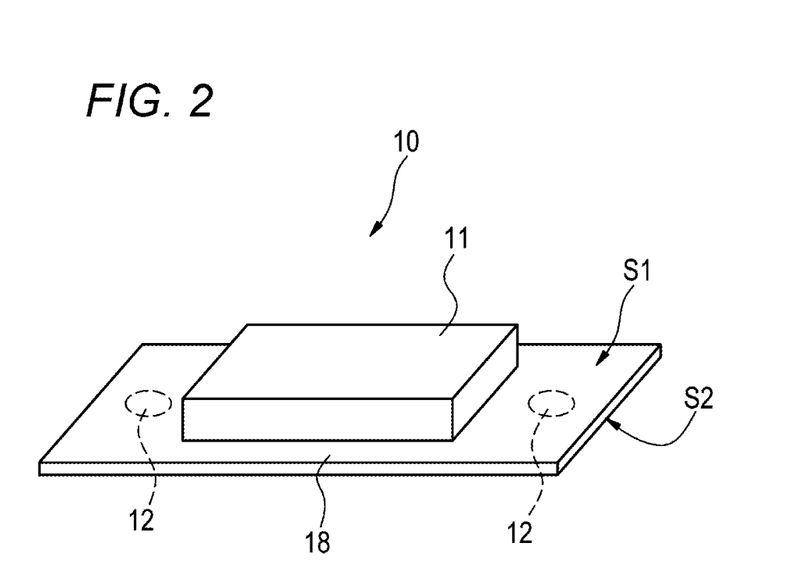
FIG. 2 is a view showing the appearance of a detection device.
Figure 3:
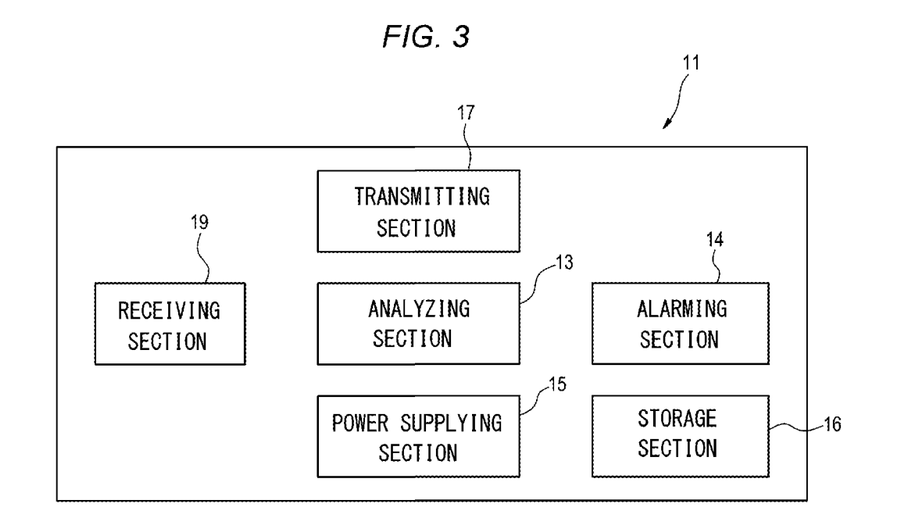
FIG. 3 is a functional block diagram of a main unit of the detection device.

As shown in FIGS. 2 and 3, the detection device 10 includes a main unit 11 and a sheet portion 18. The sheet portion 18 is, for example, a long thin sheet, and has a first face S1 and a second face S2 which is opposite to the first face S1. The main unit 11 is fixed to the first face S1, and a pair of electrodes 12 which can cooperate with the main unit 11 to function as the measuring section are fixed to the second face S2 that is opposite to the first surface S1. The second face S2 is a portion which is to be directly applied to the body surface of the user, and the outermost surface of the second face S2 is formed by an adhesive material. In a state where the second face S2 is applied to the body surface of the user, the pair of electrodes 12 function as sensor elements which can measure an electrocardiogram of the user, and are electrically connected to the main unit 11.

The main unit 11 includes a receiving section 19, an analyzing section 13, an alarming section 14, a power supplying section 15, a storage section 16, and a transmitting section 17, and is configured by, for example, a semiconductor chip dedicated to analysis of an electrocardiogram.

The receiving section 19 is connected to the analyzing section 13. The receiving section 19 can receive an electrocardiogram which is sent from the electrodes 12, and transmit the electrocardiogram to the analyzing section 13.

Figure 4:
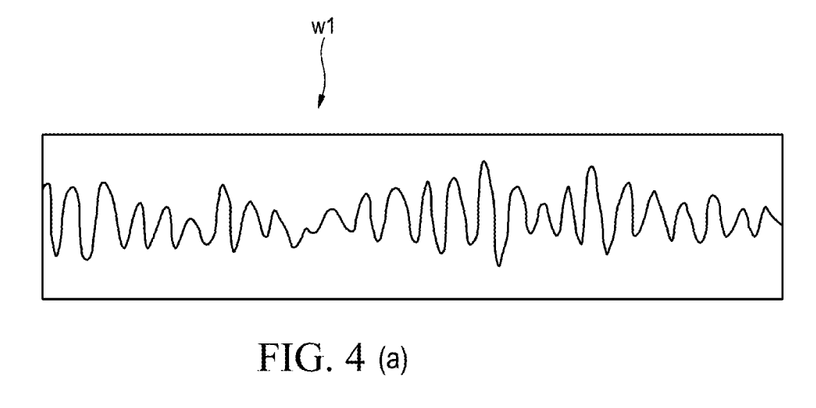
FIG. 4(a) is a view showing an example of an electrocardiogram obtained during ventricular fibrillation.
FIG. 4(b) is a view showing an example of an electrocardiogram obtained during atrial fibrillation.

The analyzing section 13 is connected to the sections in the main unit 11. For example, the analyzing section 13 can analyze whether or not an abnormal waveform indicating an arrhythmia is contained in the electrocardiogram acquired from the receiving section 19. Examples of an abnormal waveform are a waveform (see FIG. 4(a)) in an electrocardiogram which is measured during occurrence of ventricular fib-rillation W1 (VF), and a waveform (see FIG. 4(b)) in an electrocardiogram which is measured during occurrence of atrial fibrillation W2 (AF). The analyzing section 13 analyzes an electrocardiogram by using a determination algorithm which is previously designed based on characteristic factors such as excess of the heart rate per unit time over a predetermined value, and dispersions of the outline and peak interval of an abnormal waveform.

When, as a result of the analysis, an abnormal waveform is detected in the electrocardiogram under measurement, the analyzing section 13 produces a detection signal indicating that an abnormal waveform is detected. The produced detection signal is transmitted toward the alarming section 14 and the transmitting section 17.

The alarming section 14 is connected to the analyzing section 13 and the storage section 16, and functions as the speaker section which can output an alarm sound and voice message that will be described later. For example, the alarming section 14 operates in the case where the alarming section receives the detection signal.

The power supplying section 15 is connected to the sections in the main unit 11, and supplies an electric power which is necessary for operation, to the sections.

The storage section 16 is connected to the analyzing section 13 and the alarming section 14, and stores the above-described determination algorithm, alarm sounds, voice messages, etc. The alarm sounds are preferable to have a volume and tone which can cause attention of surrounding people. The voice messages include a message notifying occurrence of an arrhythmia, such as "Heart attack occurs.", that prompting rapid taking of a countermeasure, such as "Massage the heart.", that prompting a use of an automated external defibrillator (AED), such as "Find an AED in neighborhood.", and the like.

The transmitting section 17 can transmit the detection signal toward the information communication terminal 20 by using a short-range wireless communication technique such as the NFC or Bluetooth (registered trademark).

Figure 5:
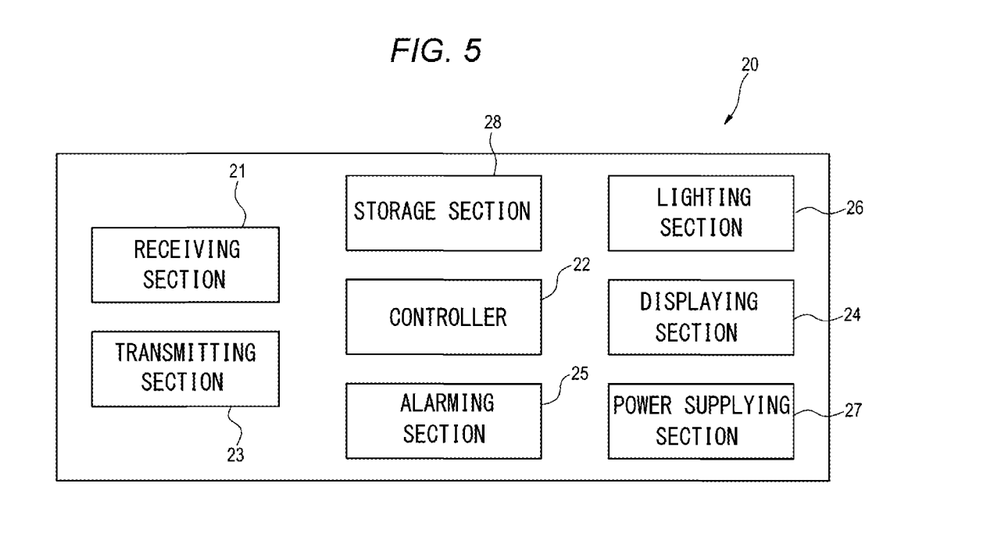
FIG. 5 is a functional block diagram of a communication terminal.

The information communication terminal 20 is a portable communication apparatus such as a smart phone or a tablet. As shown in FIG. 5, the information communication terminal 20 includes a receiving section 21, a controller 22, a transmitting section 23, a displaying section 24, an alarming section 25 (an example of the terminal alarming section), a lighting section 26, a power supplying section 27, and a storage section 28.

The receiving section 21 is connected to the controller 22, and can receive the detection signal which is wirelessly transmitted from the transmitting section 17 of the detection device 10, and then transmit the signal to the controller 22.

The controller 22 is connected to the sections in the main unit of the information communication terminal 20, and controls the operations of the sections. When the controller 22 receives the detection signal from the receiving section 21, for example, the controller can refer a transfer destination list or the like which is previously stored in the storage section 28, and instruct the transmitting section 23 to transmit the detection signal to a predetermined address(es) in the transfer destination list. The addresses of the transfer destination list include a mail address of the personal computer 30A which is owned by a family member of the user, a mail address or telephone number of the information communication terminal 30B which is owned by the family member, a mail address of a personal computer which is used by a medical person such as the attending doctor who is in charge of the user, etc.

As described above, the controller 22 can cooperate with the receiving section 21, the storage section 28, and the transmitting section 23 to function as the transferring section which automatically transfers the detection signal to other terminal apparatuses.

The displaying section 24 is connected to the controller 22 and the storage section 28, and configured by a thin touch panel display or the like. For example, the displaying section 24 can display a screen in which an operation of activating an application program stored in the information communication terminal 20 can be performed. In accordance with instructions from the controller 22 which receives the detection signal, for example, the displaying section 24 can display an alarm screen including a message indicating that an arrhythmia occurs.

The alarming section 25 is connected to the controller 22 and the storage section 28, and functions as the speaker section which can output an alarm sound and a voice message. In accordance with instructions from the controller 22 which receives the detection signal, for example, the alarming section 25 outputs an alarm sound and a voice message.

The lighting section 26 is connected to the controller 22 and the storage section 28, and functions, for example, as an alarm light which emits light in a predetermined lighting pattern. In accordance with instructions from the controller 22 which receives the detection signal, for example, the lighting section 26 repeatedly emits light of an intensity by which a person is caused to feel glare with the naked eye, in a blinking manner, thereby directing attention of a person around the information communication terminal 20 to the arrhythmia.

The power supplying section 27 is connected to the sections in the main unit of the information communication terminal 20, and supplies an electric power which is necessary for operation, to the sections.

The storage section 28 is connected to the controller 22, the displaying section 24, the alarming section 25, and the lighting section 26, and stores application programs for performing various functions, a transfer destination list which is used in the automatic transfer, the lighting pattern, alarm sounds, voice messages, etc. The alarm sounds and the voice messages may be identical with those which have been exemplified as contents to be stored in the storage section 16 of the detection device 10.

Next, an example of the operation of the alarm system 1 will be described.

Operation Example of Detection Device 10

When ventricular fibrillation occurs in the heart of the user to whom the detection device 10 is attached, the detection device 10 operates in the following manner.

In the detection device 10, the electrocardiogram sent from the electrodes 12 is analyzed by the analyzing section 13.

The analyzing section 13 analyzes the electrocardiogram by using the determination algorithm which is previously designed as described above. In the example, the analyzing section 13 detects that the electrocardiogram contains an abnormal waveform indicating an arrhythmia (ventricular fibrillation (VF)), and produces a detection signal indicating that the abnormal waveform is detected. The produced detection signal is transmitted toward the alarming section 14 and the transmitting section 17.

The alarming section 14 which receives the detection signal outputs an alarm having a volume and tone which can cause attention of surrounding people. The alarming section further outputs a voice message notifying the occurrence of an arrhythmia, such as the above-described message "Heart attack occurs."

The transmitting section 17 transmits the detection signal toward the information communication terminal 20 by using a short-range wireless communication technique such as the NFC or Bluetooth (registered trademark).

As described above, when an arrhythmia occurs in the heart of the user to whom the detection device 10 is attached, the detection device 10 detects that the electrocardiogram under measurement contains an abnormal waveform indicating an arrhythmia, and transmits the detection signal to the information communication terminal 20 which is around the user. Even when the user is in a state where the user is difficult to perform communication because of the arrhythmia, therefore, it is possible to direct attention of a person around the user to the arrhythmia, and urge the person to rapidly take a countermeasure against the arrhythmia, through the information communication terminal 20 which receives the detection signal.

According to the configuration, furthermore, it is possible to direct attention of a person around the user or the user oneself to the arrhythmia, and urge the person or the user to rapidly take a countermeasure against the arrhythmia, through the alarm sound and voice message which are output from the detection device 10 itself. Even when the occurring arrhythmia is ventricular fibrillation of high severity and urgency, and the user is, for example, in a state where the user is difficult to perform communication, it is possible to direct attention of a person around the user to the arrhythmia, and urge the person to rapidly take a countermeasure against the arrhythmia, through the alarm sound and voice message which are output from the detection device 10 itself.

Operation Example of Information Communication Terminal 20

When the information communication terminal 20 receives the detection signal from the detection device 10, the information communication terminal operates in the following manner.

Figure 6:
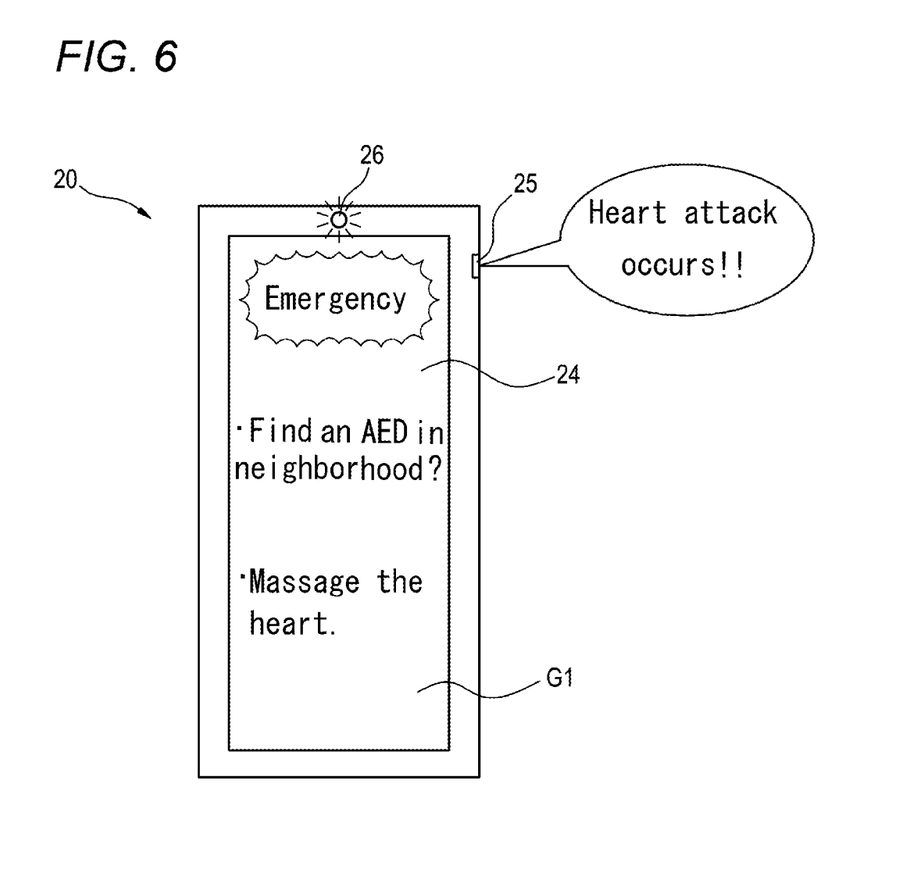
FIG. 6 is a view illustrating the operation of the alarm system.

In the information communication terminal 20, as shown in FIG. 6, the controller 22 which receives the detection signal from the receiving section 21 causes the displaying section 24 to display an alarm screen G1 including: a message calling for attention, such as "Emergency," that prompting a use of an automated external defibrillator (AED), such as "Find an AED in neighborhood.", and that prompting rapid taking of a countermeasure, such as "Massage the heart."

Moreover, the controller 22 causes the alarming section 25 to output a voice message notifying the surrounding area of the situation and calling attention, such as "Heart attack occurs!!". Furthermore, the controller 22 causes the lighting section 26 to emit light which is so strong that the light attracts attention of a surrounding person, in a blinking manner.

In parallel to the above-described operations, the controller 22 refers the transfer destination list which is previously stored in the storage section 28, and instructs the transmitting section 23 to transmit the detection signal to the terminal apparatuses 30 (30A, 30B) which are owned by the family member of the user.

As described above, the information communication terminal 20 which receives the detection signal issues an alarm sound and a voice message to the surrounding of the terminal. Even when the user is in a state where the user is difficult to perform communication because of the arrhythmia, therefore, it is possible to direct attention of a person around the user to the arrhythmia, and urge the person to rapidly take a countermeasure against the arrhythmia, through the alarm sound and voice message which are output from the information communication terminal 20. Since the alarm screen G1 is displayed on the displaying section 24, necessary information such as the situation of the user and a procedure to be performed can be correctly conveyed to a person who views the information communication terminal 20, and a rapid procedure can be further promoted.

Since the lighting section 26 is lighted, attentions of a person around the user and the user oneself can be further easily attracted, and the person or the user is urged to take more rapidly a countermeasure against the arrhythmia.

Operation Example of Terminal Apparatus 30 (30B)

When the detection signal is transferred from the information communication terminal 20, and the information communication terminal 30B owned by the family member of the user receives the detection signal, the information communication terminal 30B operates in the following manner.

Figure 7:
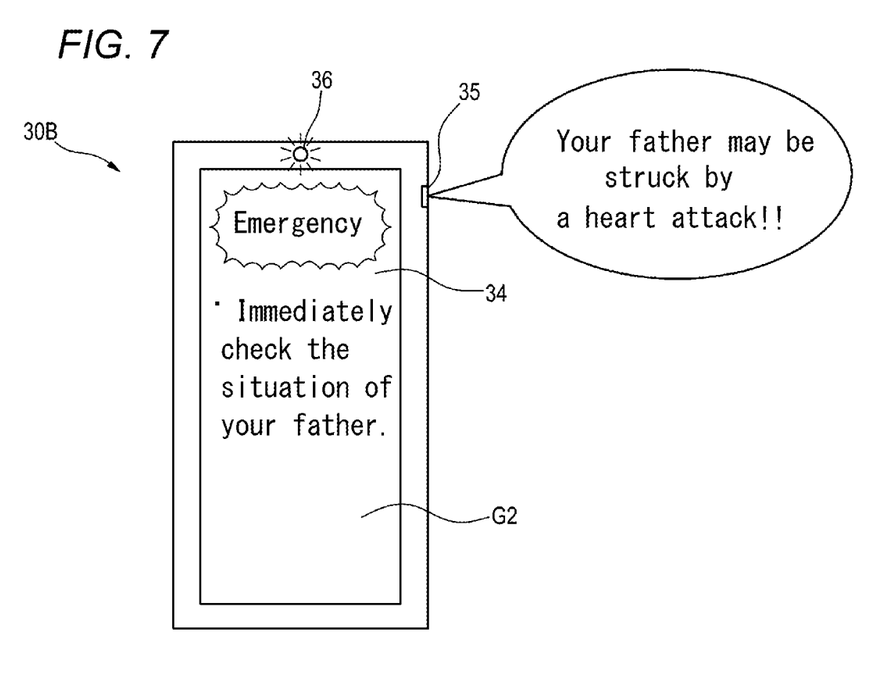
FIG. 7 is a view illustrating the operation of the alarm system.

The information communication terminal 30B is configured in a similar manner as the information communication terminal 20, and, as shown in FIG. 7, has a displaying section 34, an alarming section 35, a lighting section 36, a controller which is not shown, and the like.

In the information communication terminal 30B to which the detection signal is transferred, the displaying section 34 displays an alarm screen G2 including: a message calling for attention, such as "Emergency," and that prompting rapid taking of a countermeasure, such as "Immediately check the situation of your father."

Moreover, the alarming section 35 outputs a voice message indicating the possibility of occurrence of an emergency situation, such as "Your father may be struck by a heart attack!!". The lighting section 36 emits light which is so strong that the light attracts attention of a person carrying the information communication terminal 30B, in a blinking manner.

In the system where an automatic transfer function is provided in the information communication terminal 20, as described above, the detection signal is transferred through the information communication terminal 20 which is carried by the user in whom an arrhythmia occurs, to the information communication terminal 30B which is owned by, for example, a family member of the user. Therefore, a person such as the family member of the user who is remote from the user can rapidly know that an arrhythmia occurs. Alternatively, the detection signal may be transferred to terminal apparatuses 30 respectively owned by a plurality of persons (such as a medical person), in addition to terminal owned by the family member.

Although the above operation example has been described under assumption that ventricular fibrillation occurs in the heart of the user to whom the detection device 10 is attached, the invention is not limited to the example. Also when atrial fibrillation which is relatively lower in urgency than ventricular fibrillation occurs, for example, the invention can be applied. In the case of atrial fibrillation, for example, a character message "Occurrence of atrial fibrillation is suspected. Please get a diagnosis in a hospital." may be displayed in the alarm screen. The character message may be output as a voice message. With respect to the automatic transfer function, similarly with the case of ventricular fibrillation, the detection signal may be transferred to terminal apparatuses 30 of a plurality of persons (such as a medical person), and the health status of the user may be shared.

According to the configuration, with respect to an atrial fibrillation which is relatively hardly felt by the user oneself as compared to ventricular fibrillation, it is possible to direct attention of a person around the user or the user oneself to the atrial fibrillation, and urge the person or the user to rapidly take a countermeasure against the atrial fibrillation.

Examples of an arrhythmia are not limited to ventricular fibrillation and atrial fibrillation. The invention can be applied to any kind of disease as far as the disease exhibits a symptom of a type in which the kind of an abnormal waveform can be automatically determined relatively accurately by analyzing the waveform of an electrocardiogram.

Modification 1

Figure 8:
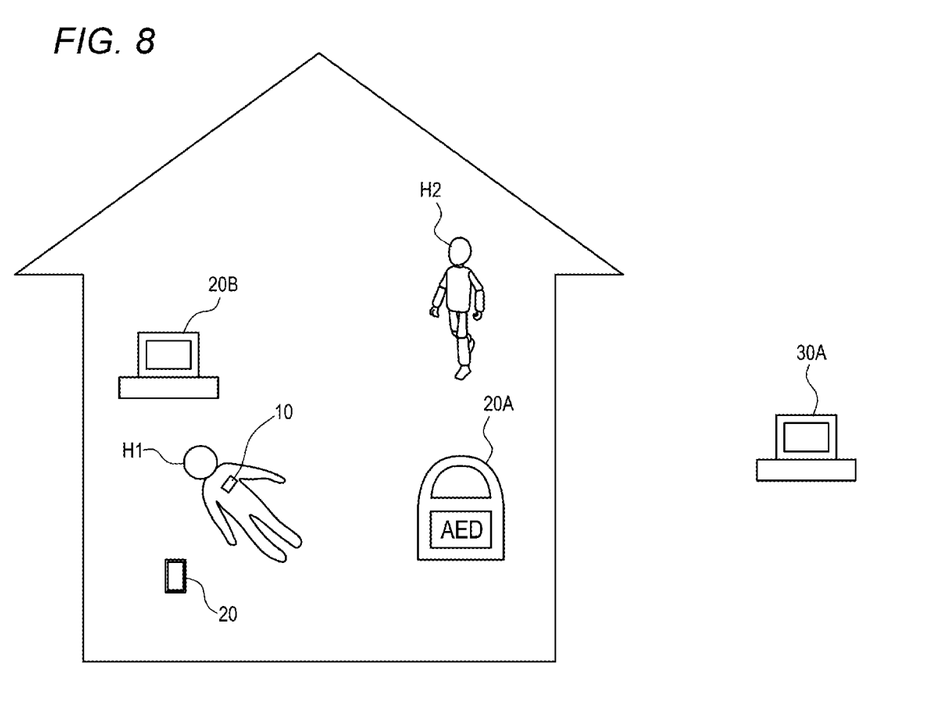
FIG. 8 is a diagram showing a modification of the alarm system.

Although, in the above-described embodiment, the information communication terminal 20 of the user is exemplified as a terminal to which the detection device 10 directly transmits the detection signal, the invention is not limited to the embodiment. As shown in FIG. 8, for example, the detection device 10 may be configured so as to wirelessly transmit a detection signal to an automated external defibrillator (AED) 20A, an activity measuring apparatus 20B, and an indoor alarming apparatus (not shown) such as a fire alarming apparatus.

The automated external defibrillator 20A is disposed in, for example, the house of the user H1, and is configured so as to be able to receive the detection signal from the detection device 10. The automated external defibrillator 20A which receives the detection signal can operate in a similar manner as the information communication terminal 20, and can output, to the surrounding area, a voice message calling for attention, such as "Emergency," that informing of the location of the automated external defibrillator 20A, such as "An AED is here!", and that prompting rapid taking of a countermeasure, such as "Massage the heart." The automated external defibrillator 20A may have a lighting section, and emit light which is so strong that the light attracts attention of a surrounding person, in a blinking manner. The output from the AED enables the situation to be immediately understood, and eliminates the labor of searching the AED. Therefore, the modification exerts outstanding effects on rapid treatment.

According to the configuration, the automated external defibrillator 20A outputs the voice message or the like informing of the location where the defibrillator 20A is disposed. Therefore, a housemate H2 can easily find the automated external defibrillator 20A according to the direction of the sound or the contents of the voice message, and rapidly take a countermeasure by using the automated external defibrillator 20A.

The activity measuring apparatus 20B is disposed in the house of the user H1, and configured so as to be able to receive the detection signal from the detection device 10. The activity measuring apparatus 20B has a sensor for measuring the activity of the user H1, and is communicably connected to the personal computer 30A which is used by a medical person, security personnel, or family member who monitors the activity of the user H1, through a network such as the Internet.

The activity measuring apparatus 20B can operate in a similar manner as the information communication terminal 20, and output, to the surrounding area, an alarm sound, a voice message calling for attention, such as "Emergency," that prompting rapid taking of a countermeasure, such as "Massage the heart.", and the like. Similarly with the information communication terminal 20, the activity measuring apparatus 20B may transfer the detection signal to the personal computer 30A. The personal computer 30A which receives the detection signal may output a voice message indicating the possibility of occurrence of an emergency situation, such as "The user may be struck by a heart attack!!", or display an equivalent character message on a display screen.

According to the configuration, an alarm sound and a voice message can be output from the activity measuring apparatus 20B and the indoor alarming apparatus (not shown) such as a fire alarming apparatus, and therefore the housemate H2 can be quickly informed of the occurrence of an arrhythmia. Moreover, the transfer to the personal computer 30A enables a medical person, security personnel, or the like who performs remote monitoring can rapidly know that an arrhythmia occurs.

Modification 2

Figure 9:
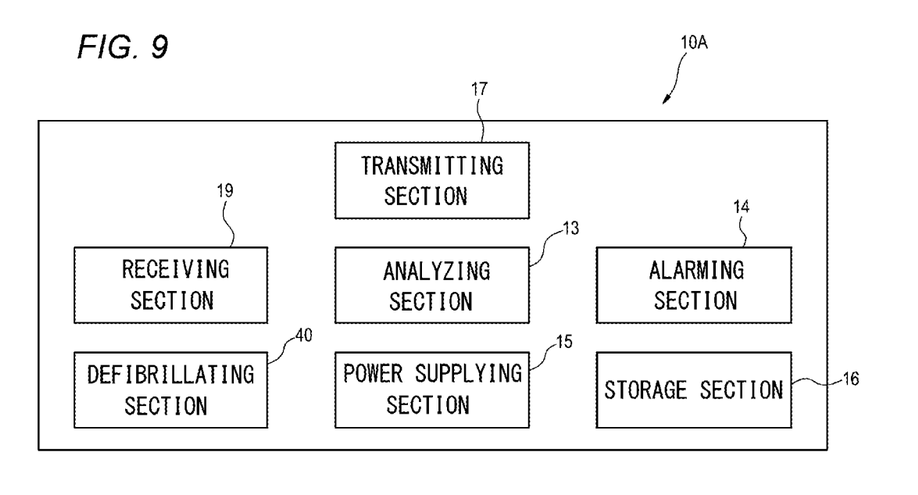
FIG. 9 is a functional block diagram showing a modification of the detection device.

FIG. 9 shows a detection device 10A which is a modification of the detection device 10. The detection device 10A is different from the detection device 10 in that the detection device 10A has a defibrillating section 40, and similar in the other configuration.

The defibrillating section 40 is connected to the analyzing section 13 and the power supplying section 15. The defibrillating section 40 which receives the detection signal can cooperate with the power supplying section 15 to produce an electrical simulation for defibrillation of ventricular fibrillation, and apply the electrical simulation to the user through the electrodes 12.

According to the configuration, defibrillation can be rapidly performed on the occurring ventricular fibrillation.

Modification 3

Figure 10:
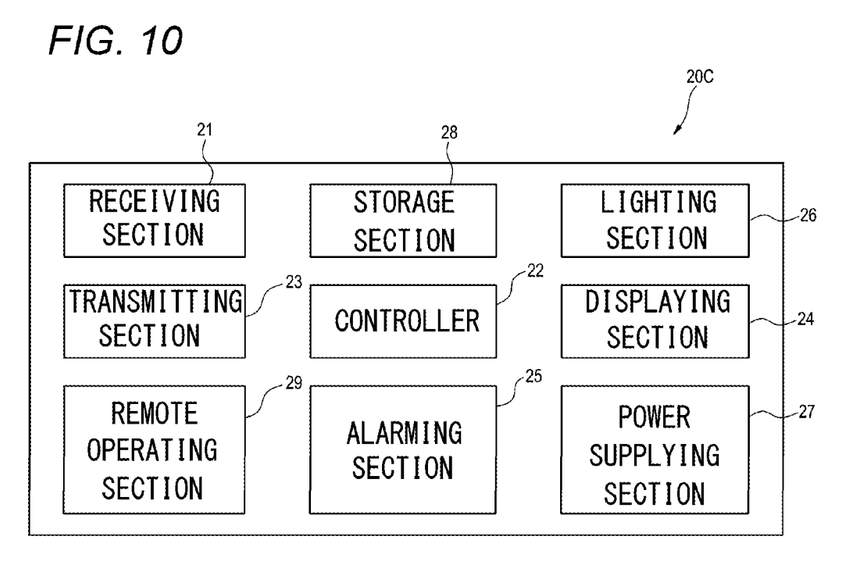
FIG. 10 is a functional block diagram showing a modification of the communication terminal.
Figure 11:
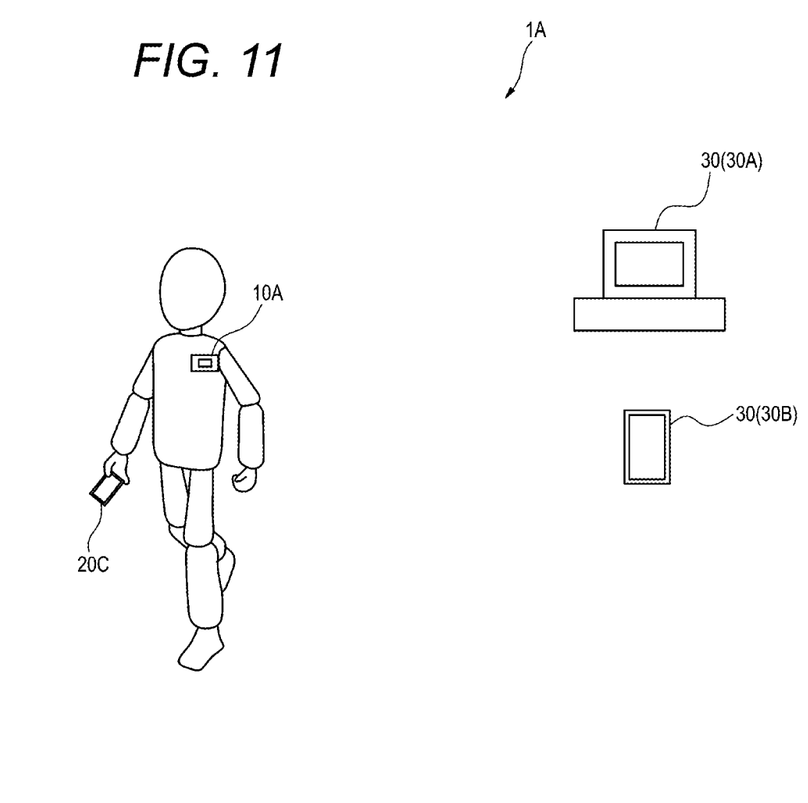
FIG. 11 is a diagram showing another modification of the alarm system.

FIG. 10 shows an information communication terminal 20C as a modification of the information communication terminal 20 which is an example of the communication terminal. The information communication terminal 20C is different from the information communication terminal 20 in that the terminal 20C has a remote operating section 29, and similar in the other configuration. FIG. 11 shows an alarm system 1A including: the detection device 10A having the defibrillating section 40; the information communication terminal 20C having the remote operating section 29; and the terminal apparatuses 30. The alarm system 1A is configured so that the detection device 10A is bidirectionally communicable with the information communication terminal 20C and the terminal apparatuses 30.

As described above, the information communication terminal 20C has the remote operating section 29. The remote operating section 29 is connected to the controller 22 and the transmitting section 23, and functions as an operating section for remotely operating the detection device 10A. As shown in FIG. 12, for example, the remote operating section 29 is configured as an operation screen 29A (Turn ON defibrillation) for activating the defibrillating section 40 of the detection device 10A, on the touch panel display of the displaying section 24.

OPERATION EXAMPLES

In the information communication terminal 20C which receives the detection signal indicating that an abnormal waveform is detected, from the detection device IDA, for example, the operation screen 29A is displayed on the alarm screen G1 of the displaying section 24. In the case where a person who views the information communication terminal 20C determines that defibrillation is necessary, according to other information displayed on the alarm screen G1, and the condition of the user, the person can operate the operation screen 29A. When the operation screen 29A is operated, an operation signal instructing the defibrillating section 40 to be activated is transmitted from the information communication terminal 20C to the detection device 10A. The detection device IDA which receives the operation signal causes the defibrillating section 40 to be activated, based on the operation signal, cooperates with the power supplying section 15 to produce an electrical simulation for defibrillation of ventricular fibrillation, and applies the electrical simulation to the user through the electrodes 12.

According to the configuration, even in the case where the automatic activation of the defibrillating section 40 fails on the side of the detection device 10A, when a person who views the information communication terminal 20C operates the operation screen 29A according to other information displayed on the alarm screen G1, and the condition of the user, it is possible to remotely activate the defibrillating section 40 of the detection device 10A.

Alternatively, the remote operating section 29 may be configured by the information communication terminal 20C and any one of the terminal apparatuses 30. In other words, a communication terminal having the remote operating section 29 may be configured by the information communication terminal 20C and the terminal apparatus 30. In the alternative, an operation signal instructing the defibrillating section 40 to be activated may be produced by using an input interface such as a keyboard of the terminal apparatus 30A or the touch panel display of the terminal apparatus 30B, and then transmitted to the detection device 10A through the information communication terminal 20C.

Microphone portions which are provided in the terminal apparatuses 30 and the information communication terminal 20C may be configured as a remote operating section. For example, a voice message which is input in the microphone portion of one of the terminal apparatuses 30 may be transmitted to the detection device 10A through the information communication terminal 20C, and output from the speaker section of the detection device 10A. Alternatively, a voice message which is input in the microphone portion of the information communication terminal 20C may be transmitted to the detection device 10A, and output from the speaker section of the detection device 10A.

Alternatively, the electrocardiogram which is measured by the detection device 10A, and a result of the analysis which is performed by the analyzing section 13 may be transmitted from the detection device 10A to the terminal apparatuses 30 through the information communication terminal 20C, and displayed on the displaying sections of the terminal apparatuses 30. In the alternative, the detection device 10A is remotely operated from one of the terminal apparatuses 30 to acquire the electrocardiogram and the analysis result. A configuration may be employed in which the electrocardiogram which is measured by the detection device 10A, and a result of the analysis which is performed by the analyzing section 13 is displayed on the displaying section 24 of the information communication terminal 20C.

As described above, when the detection device 10A is bidirectionally communicable with the information communication terminal 20C and the terminal apparatuses 30 so that the detection device 10A can be remotely operated, the occurring arrhythmia can be rapidly coped with the occurring arrhythmia by various methods.

The invention is not limited to the embodiment and modifications which have been described, and may be adequately subjected to modification, improvement, and the like. In addition, the materials, shapes, dimensions, numerical values, forms, numbers, placement places, and the like of the components of the above-described embodiment are arbitrary and not limited insofar as the invention is achieved.

Although the examples have been described in which the detection device (10, 10A) is configured by the main unit 11 and the sheet portion 18 which is to be applied to the body surface of the user, and the components such as the receiving section 19, the analyzing section 13, the alarming section 14, the power supplying section 15, the storage section 16, and the transmitting section 17 are disposed in the main unit 11, the invention is not limited to the examples. For example, the functions other than those of the receiving section 19 and transmitting section 17 which cooperate with the electrodes 12 of the sheet portion 18 applied to the body surface of the user to function as the measuring section may be disposed in another device (component) which is separated from the main unit 11. A device in which separated partial functions are disposed may employ a form in which the device is not to be applied to the body surface of the user, such as a form in which the device can be housed in a pocket of the clothes of the user, that in which the device is carried by the user while being hooked to the belt wound around the waist of the user, or that in which the device is attached to a pendant worn by the user. The device, the main unit 11, and the sheet portion 18 can integrally operate to exert the above-described function of the above-described detection device.

The present application is based on Japanese Patent Application No. 2016-050647 filed on Mar. 15, 2016, Japanese Patent Application No. 2016-102663 filed on May 23, 2016 and Japanese Patent Application No. 2017-020727 filed on Feb. 7, 2017, the entire contents of which are incorporated herein by reference.

What is claimed is:

1. An alarm system including:
a detection device which is a portable detection device, the detection device including a main unit and a sheet portion, the main unit being fixed on the sheet portion such that a surface of the main unit is exposed outwards in a state where the detection device is applied to a body surface of a user; and
an automated external defibrillator which is communicable with the detection device,
wherein the main unit includes:
a measuring section which can measure an electrocardiogram in a state where the measuring section is applied to the body surface of the user,
an analyzing section which analyzes whether the electrocardiogram contains an abnormal waveform indicating an arrhythmia or not, and
a transmitting section which, if the analyzing section detects the abnormal waveform, transmits a detection signal indicating that the abnormal waveform is detected, to the automated external defibrillator around the user,
wherein the sheet portion has a sheet shape in which the device is portable in a state where the sheet portion is applied to the body surface of the user, and at least one part of a surface of the sheet portion is formed by an adhesive material,
wherein the automated external defibrillator has:
a receiving section which receives the detection signal transmitted from the transmitting section of the detection device, and
a transferring section which automatically transfers the detection signal to a plurality of other terminal apparatuses by referring to a transfer destination list which is previously stored and sending the detection signal to predetermined addresses in the transfer destination list, and
wherein when the automated external defibrillator receives the detection signal, the automated external defibrillator is configured to perform at least one from the group consisting of:
outputting a message informing of a location of the automated external defibrillator,
outputting a message prompting taking of a countermeasure for the user, and
emitting light in a blinking manner using a lighting section.

2. The alarm system according to claim 1, wherein the main unit further includes a main unit alarming section which, if the abnormal waveform is detected, issues a main unit alarm.

3. The alarm system according to claim 2, wherein the main unit alarm includes a voice message indicating that an arrhythmia occurs.

4. The alarm system according to claim 1, wherein:
the arrhythmia is ventricular fibrillation or atrial fibrillation,
the abnormal waveform is a waveform indicating ventricular fibrillation or atrial fibrillation, and
the analyzing section analyzes whether the abnormal waveform indicating ventricular fibrillation or atrial fibrillation is contained in the electrocardiogram or not.

5. The alarm system according to claim 4, wherein the main unit further includes:
a defibrillating section which, if the abnormal waveform is detected, applies an electrical simulation for defibrillation to the user; and
a power supplying section which can supply an electric power necessary for the defibrillation.

6. The alarm system according to claim 1, wherein the transmitting section transmits the detection signal to an indoor alarming apparatus which issues an indoor alarm or a voice message when the detection signal from transmitting section of the detection device is received.

7. The alarm system according to claim 1, wherein the automated external defibrillator includes a remote operating section which remotely operates the detection device.

8. The alarm system according to claim 7, wherein the main unit further includes:
a defibrillating section which, if the abnormal waveform is detected, applies an electrical simulation for defibrillation to the user; and
a power supplying section which can supply an electric power necessary for the defibrillation,
wherein the remote operating section operates the defibrillating section of the detection device to apply the electrical simulation to the user of the detection device.

9. The alarm system according to claim 7, wherein:
the main unit of the detection device further includes a speaker section, and
a sound which is input to the remote operating section is output through the speaker section.

10. The alarm system according to claim 1, wherein the automated external defibrillator includes a displaying section which displays the electrocardiogram measured by the measuring section, or a result of the analysis performed by the analyzing section.

11. The alarm system according to claim 1, wherein:
the sheet portion has a first surface and a second surface opposite to the first surface,
the main unit is fixed on the first surface of the sheet portion, and
at least one part of the second surface of the sheet portion is formed by the adhesive material.

12. An alarm system including:
a detection device which is a portable detection device, the detection device including a main unit and a sheet portion; and
an automated external defibrillator which is communicable with the detection device,
wherein the main unit includes:
a measuring section which can measure an electrocardiogram in a state where the measuring section is applied to a body surface of a user,
an analyzing section which analyzes whether the electrocardiogram contains an abnormal waveform indicating an arrhythmia or not, a transmitting section which, if the analyzing section detects the abnormal waveform, transmits a detection signal indicating that the abnormal waveform is detected, to the automated external defibrillator around the user, and a main unit alarming section which, if the abnormal waveform is detected, issues a main unit alarm, wherein the sheet portion has a sheet shape in which the device is portable in a state where the sheet portion is applied to the body surface of the user, and at least one part of a surface of the sheet portion is formed by an adhesive material, wherein the automated external defibrillator has:

a receiving section which receives the detection signal transmitted from the transmitting section of the detection device, and a transferring section which automatically transfers the detection signal to a plurality of other terminal apparatuses by referring to a transfer destination list which is previously stored and sending the detection signal to predetermined addresses in the transfer destination list, and wherein when the automated external defibrillator receives the detection signal, the automated external defibrillator is configured to perform at least one from the group consisting of:

outputting a message informing of a location of the automated external defibrillator, outputting a message prompting taking of a countermeasure for the user, and emitting light in a blinking manner using a lighting section.

13. The alarm system according to claim 12, wherein the main unit alarming section is supported by the sheet portion.

14. An alarm system including:

a detection device which is a portable detection device, the detection device including a main unit and a sheet portion, the main unit being fixed on the sheet portion such that a surface of the main unit is exposed outwards in a state where the detection device is applied to a body surface of a user; and an automated external defibrillator which is communicable with the detection device, wherein the main unit includes:

a measuring section which can measure an electrocardiogram in a state where the measuring section is applied to the body surface of the user, an analyzing section which analyzes whether the electrocardiogram contains an abnormal waveform indicating an arrhythmia or not, and a transmitting section which, if the analyzing section detects the abnormal waveform, transmits a detection signal indicating that the abnormal waveform is detected, to the automated external defibrillator around the user, wherein the automated external defibrillator has a receiving section which receives the detection signal transmitted from the transmitting section of the detection device, and wherein when the automated external defibrillator receives the detection signal, the automated external defibrillator is configured to perform at least one from the group consisting of:

outputting a message informing of a location of the automated external defibrillator, outputting a message prompting taking of a countermeasure for the user, and emitting light in a blinking manner using a lighting section.

* * * * *

UNITED STATES PATENT AND TRADEMARK OFFICE
CERTIFICATE OF CORRECTION

| | |
|---|---|
| PATENT NO. | : 11,253,716 B2 |
| APPLICATION NO. | : 16/079748 |
| DATED | : February 22, 2022 |
| INVENTOR(S) | : Ogino et al. |

It is certified that error appears in the above-identified patent and that said Letters Patent is hereby corrected as shown below:

In the Specification

Column 9, Line 45, "detection device IDA, for" should read -- detection device 10A, for --

Signed and Sealed this
Nineteenth Day of July, 2022

Katherine Kelly Vidal
*Director of the United States Patent and Trademark Office*